(12) United States Patent
Malakan Rad et al.

(10) Patent No.: US 11,197,660 B2
(45) Date of Patent: Dec. 14, 2021

(54) ASYMMETRIC OCCLUDER DEVICE

(71) Applicant: Occlutech Holding AG, Schaffhausen (CH)

(72) Inventors: Elaheh Malakan Rad, Tehran (IR); Ziyad Mousa Hijazi, San Diego, CA (US)

(73) Assignee: Occlutech Holding AG, Schaffhausen (CH)

(*) Notice: Subject to any disclaimer, the term of this patent is extended or adjusted under 35 U.S.C. 154(b) by 72 days.

(21) Appl. No.: 16/120,195

(22) Filed: Aug. 31, 2018

(65) Prior Publication Data

US 2018/0368820 A1 Dec. 27, 2018

Related U.S. Application Data

(63) Continuation of application No. 14/292,033, filed on May 30, 2014, now Pat. No. 10,064,612.
(Continued)

(51) Int. Cl.
*A61B 17/00* (2006.01)
*A61L 31/02* (2006.01)
*A61L 31/04* (2006.01)

(52) U.S. Cl.
CPC ........ *A61B 17/0057* (2013.01); *A61L 31/022* (2013.01); *A61L 31/04* (2013.01);
(Continued)

(58) Field of Classification Search
CPC .......... A61B 17/12036; A61B 17/1204; A61B 17/12099; A61B 17/12131;
(Continued)

(56) References Cited

U.S. PATENT DOCUMENTS 5,944,738 A * 8/1999 Amplatz ............ A61B 17/0057
606/213
6,468,303 B1 * 10/2002 Amplatz ................ A61B 17/11
623/1.2
(Continued)

FOREIGN PATENT DOCUMENTS

WO WO2008/040555 A2 4/2008

OTHER PUBLICATIONS

Abaci, Adnan, M.D. et al., "Short and Long Term Complications of Device Closure of Atrial Septal Defect and Patent Foramen Ovale: Meta-Analysis of 28,142 Patients from 203 Studies," *Catheterization and Cardiovascular Interventions*, Feb. 14, 2013, 82:1123-1138, 16 pages.
(Continued)

*Primary Examiner* — Diane D Yabut
(74) *Attorney, Agent, or Firm* — Inskeep IP Group, Inc.

(57) ABSTRACT

An asymmetric occlusion device for occluding an opening in a body tissue where part of the opening is defined by a partial inadequate rim. The asymmetric occlusion device includes a waist portion having a distal end extending to a proximal end. The waist portion is of non-woven material extending around a longitudinal axis opening. The occlusion device further includes a pair of asymmetric occluder disks attached to the waist. The asymmetric distal and proximal occluder disks are formed of shape memory material. The asymmetric occluder disks include a short arm extending from the waist and an extended arm extending from the waist. The extended arm exceeds the length of the first short arm. The density of the first short arm exceeds the density of the second extended arm.

4 Claims, 8 Drawing Sheets

Related U.S. Application Data (60) Provisional application No. 61/828,991, filed on May 30, 2013.

(52) U.S. Cl.
CPC .............. *A61B 2017/00358* (2013.01); *A61B 2017/00575* (2013.01); *A61B 2017/00592* (2013.01); *A61B 2017/00606* (2013.01); *A61B 2017/00623* (2013.01); *A61B 2017/00867* (2013.01); *A61B 2017/00876* (2013.01)

(58) Field of Classification Search
CPC ........ A61B 17/12045; A61B 17/12109; A61B 17/12031; A61B 17/12122; A61B 17/12113; A61B 2017/12127; A61B 2017/00641; A61B 2017/00592; A61B 2017/00619; A61B 2017/00646; A61B 2017/00623; A61B 2017/1205; A61B 2017/00575; A61B 17/0057; A61B 17/12022; A61B 17/12027; A61B 17/12118; A61B 17/1214; A61B 17/12145; A61B 17/1215; A61B 17/12154; A61B 17/12163; A61B 17/12168; A61B 17/12172; A61B 17/112177; A61B 2017/00597; A61B 2017/00606; A61B 2017/00632; A61B 2017/00637

See application file for complete search history.

(56) References Cited

U.S. PATENT DOCUMENTS

| | | | |
|---|---|---|---|
| 2004/0098121 | A1 | 5/2004 | Opolski |
| 2006/0136043 | A1 | 6/2006 | Cully et al. |
| 2006/0224183 | A1 | 10/2006 | Freudenthal |
| 2008/0200945 | A1 | 8/2008 | Amplatz et al. |
| 2009/0171386 | A1* | 7/2009 | Amplatz .......... A61B 17/12122 606/213 |
| 2009/0228038 | A1 | 9/2009 | Amin |
| 2009/0312789 | A1 | 12/2009 | Kassab et al. |
| 2010/0204662 | A1 | 8/2010 | Orlov et al. |
| 2011/0054519 | A1 | 3/2011 | Neuss |
| 2012/0071918 | A1 | 3/2012 | Amin et al. |
| 2014/0039543 | A1 | 2/2014 | Willems et al. |

OTHER PUBLICATIONS

Srilatha Alapati, Srilatha et al., "Historical Aspects of Transcatheter Occlusion of Atrial Septal Defects," *Atrial Septal Defect*, Dr. P. Syamasundar Rao (Ed.), ISBN: 978-953-51-0531-2, *InTech*, Available from: http://www.intechopen.com/books/atrial-septal-defect/historical-aspects-of-transcatheter-occlusion-of-atrial-septal-defects, Apr. 25, 2012, 30 pages.

Amin, Zahid, "Transcatheter Closure of Secundum Atrial Septal Defects," *Catheterization and Cardiovascular Interventions*, 68:778-787, Oct. 25, 2006, 10 pages.

Chan, Kam Tim, et al., "Retrieval of an Embolized Amplatzer Septal Occluder," *Catheterization and Cardiovascular Interventions*, 75:465-468, Feb. 15, 2010, 4 pages.

Fischer, G., et al., "Transcatheter closure of secundum atrial septal defects with the new self-centering Amplatzer Septal Occluder," *European Heart Journal*, 20:541-549, Apr. 1, 1999, 9 pages.

Gokaslan, Gokhan, et al., "Urgent surgical management for embolized occlude devices in childhood: single center experience," *Journal of Cardiothoracic Surgery* 2012, 7:127, Dec. 7, 2012, 7 pages.

Kannan, Bhava Ramalingam Jawahar, M.D., et al., "Transcatheter Closure of Very Large (≥25 mm) Atrial Septal Defects Using the Amplatzer Septal Occluder," *Catheterization and Cardiovascular Interventions*, 59: 522-527, Jul. 23, 2003, 6 pages.

Kazmouz, Suhaib, M.D., et al., "Transcatheter Closure of Secundum trial Septal Defects," *J Invasive Cardiol*, 25(5);257-264, May 2013, 8 pages.

King, Terry Dean, et al., "Chapter 4: Historical perspectives on ASD device closure," *Transcatheter Closure of ADSs and PFOs, a Comprehensive Assessment*, Hijazi, Ziyad J. M.D et al., eds., Cardiotext Publishing; Jul. 30, 2010, pp. 27-63, 28 pages.

King, Terry D., et al., "Secundum Atrial Septal Defect, Nonoperative Closure During Cardiac Catheterization," *JAMA* 235:2506-2509, Jun. 7, 1976, 4 pages.

Knirsch, W., et al., "Challenges Encountered During Closure of Atrial Septal Defects," *Pediatr Cardiol*, 26:147-153, Mar.-Apr. 2005, 7 pages.

Levi, Daniel S., M.D., et al., "Embolization and Retrieval of the Amplatzer Septal Occluder," *Catheterization and Cardiovascular Interventions*, 61:543-547, Mar. 29, 2004, 5 pages.

Li, Sui-Shuang, et al., "Feasibility and Safety of Transthoracic Echocardiography-Guided Transcatheter Closure of Atrial Septal Defects with Deficient Superior-Anterior Rims," *PLoS One*, 7(12) e511117, Dec. 17, 2012, 7pages.

Love, Barry A., M.D., et al., "Advantages of the GORE® HELEX® Septal Occluder for Closure of Atrial Septal Defect with a Deficient Retroaortic Rim," *Gore Medical Closing Remarks Newsletter*, goremedical.com/HELEX, Summer 2012, Issue XIX, 8 pages.

Moore, John, M.D., et al., "Transcatheter Device Closure of Atrial Septal Defects," *JACC: Cardiovascular Interventions*, vol. 6, Issue 5, May 2013, pp. 433-442, 10 pages.

Ohno, Naoki, M.D., et al., "Characteristics of Secundum Atrial Septal Defects Not Percutaneously Closed," *Catheterization and Cardiovascular Interventions*, 2014 85(2) Oct. 29, 2014, 6 pages.

Papa, Marco, M.D., et al., "Feasibility and Safety of Transcatheter Closure of Atrial Septal Defects with Deficient Posterior Rim," *Catheterization and Cardiovascular Intervention*, 81:1180-1187, Jun. 1, 2013, 8 pages.

Podnar, Tomaž, M.D., et al., "Morphological Variations of Secundum-Type Atrial Septal Defects: Feasibility for Percutaneous Closure Using Amplatzer Septal Occluders," *Catheterization and Cardiovascular Intervention*, 53:386-391, Jun. 29, 2001, 6 pages.

Vaidyanathan, Balu, DM, et al., "Transesophageal Echocardiography for Device Closure of Atrial Septal Defects, Case Selection, Planning, and Procedural Guidance," *JACC: Cardiovascular Imaging*, vol. 2, No. 10, Oct. 1, 2009, pp. 1238-1242, 5 pages.

Yared, Kibar, M.D., et al., "Echocardiographic Assessment of Percutaneous Patent Foramen Ovale and Atrial Septal Defect Closure Complications," *Circulation: Cardiovascular Imaging*, 2:141-149, Mar. 1, 2009, 10 pages.

\* cited by examiner

ASYMMETRIC OCCLUDER DEVICE

RELATED APPLICATIONS

The application is a continuation of and claims priority to U.S. patent application Ser. No. 14/292,033 filed May 30, 2014, now U.S. Pat. No. 10,064,612, entitled Asymmetric Occluder Device, which claims benefit of and priority to U.S. Provisional Application No. 61/828,991 filed May 30, 2013 entitled Asymmetric Occluder For Transcatheter Atrial Septal Defect Closure In Patients With Secundum Atrial Septal Defect And Inadequate Rims, both of which are incorporated herein by reference in their entireties.

BIBLIOGRAPHY

Complete bibliographical citations to the documents cited herein can be found in the Bibliography, immediately preceding the claims.

FIELD OF THE INVENTION

The present invention is directed to a medical device and particularly to a device for closing or occluding atrial septal defects in patients with secundum atrial septal defect and inadequate rims.

BACKGROUND

Atrial septal defect (ASD) is one of the most common congenital heart defects, accounting for 7%-10% of all congenital Heart disease in children and 30%-33% of defects diagnosed in adults With congenital heart disease (Kazmouz et al. 2013). Secundum atrial septal defect (ASD) is a congenital heart defect in the septum between the atria of the heart, which allows blood to flow from the left atrium to the right atrium through a hole or defect in the interatrial septum. This defect is typically caused by deficiency of valve tissue of fossa ovalis, excessive or ectopic resorption of septum primum or deficient growth of septum secundum. Forty years ago, Dr. Terry D. King performed the first transcatheter closure of atrial septal defect using double umbrella disks (King et al. 1976). Since then, many devices have been developed to close such defects (King and Mills 2010). During a cardiac catheterization, a thin catheter is inserted into a blood vessel in the groin of a patient and guided to the heart. Through the catheter, a mesh patch or plug is put into place to close to close the interatrial defect. The heart tissue grows around the mesh permanently sealing the defect.

However, patients With ASD and inadequate rims are not good candidates for the available devices or may pose significant technical challenges seating the device well (Podnar et al. 2001; Amin 2006; Kannan, et al. 2003). An inadequate rim of tissue around the ASD may not allow for proper device anchoring leading to device malposition. The most common site of deficient rim is the retroaortic area (also called the anterior-superior rim) which may be deficient in up to 45% of patients With ASD (Knirsch et al., 2005; cited in Love, et al., 2012).

Therefore, currently, many of these patients are referred for traditional surgical closure of their defects (Moore et al. 2013; Gokaslan et al. 2012). However, an inadequate rim is one of the serious challenges for transcatheter closure of ASD, making this treatment modality impossible in many occasions (Li et al. 2012). The purpose of this invention is to modify these defects (defects With deficient or inadequate rims) and to make their defects more feasible for transcatheter closure.

SUMMARY OF THE INVENTION

The present invention is directed to a heart occluder device comprising two separate, uniquely—shaped members separated by a middle portion or waist wherein each member is shaped into two semi-ovoid designs to form two half-discs by the memory—shaping capability of the Wires forming the members. The waist area is formed between the two semi—ovoid designs.

The present invention is further directed to an asymmetric occlusion device for occluding an opening in a body tissue wherein the opening is defined by a partial adequate rim and a partial inadequate rim. The asymmetric occlusion device comprises a waist portion having a distal end extending to a proximal end, the waist portion being formed of non-woven material extending around a longitudinal axis opening. The occlusion device further includes a pair of asymmetric occluder disks, comprising an asymmetric distal occluder disk attached to the distal portion of the waist, the asymmetric distal occluder disk being made of shape memory material, and an asymmetric proximal occluder disk attached to the proximal portion of the waist, the asymmetric proximal occluder disk being made of shape memory material. The asymmetric occluder disks are defined by a first short arm extending from the waist wherein the first short arm includes shape memory material, and a second extended arm extending from the waist, wherein the second extended arm exceeds the length of the first short arm and wherein the second long arm includes shape memory material, wherein the density of the first short arm exceeds the density of the second extended arm.

The present invention is further directed to an asymmetric atrial septum occlusion device for occluding an atrial septum defect, wherein the atrial septum defect is defined by a partial adequate rim and a partial inadequate rim. The occlusion device comprises a waist portion having a distal end extending to a proximal end, the waist portion being formed of non-woven material extending around a longitudinal axis opening, wherein the waist comprises a hub and a channel passing through the hub. The occlusion device further includes a pair of ovoid asymmetric occluder disks, comprising an asymmetric distal occluder disk attached to the distal portion of the waist, the asymmetric distal occluder disk being made of shape memory material, and an asymmetric proximal occluder disk attached to the proximal portion of the waist, the asymmetric proximal occluder disk being made of shape memory material, wherein the distal disk is larger in size than the proximal disk to prevent dislodgement of the occluder device from the body tissue opening, wherein further the asymmetric occluder disks comprise a first short arm extending from the waist wherein the first short arm includes shape memory material, and a second extended arm extending from the waist, wherein the second extended arm exceeds the length of the first short arm and wherein the second long arm includes shape memory material. The density of the first short arm exceeds the density of the second extended arm.

The design and deployment of this device is easy and very similar to conventional Amplatzer ASD occluder.

The objects and advantages of the invention will appear more fully from the following detailed description of the preferred embodiment of the invention made in conjunction with the accompanying drawings.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DETAILED DESCRIPTION OF THE INVENTION

The present invention provides a device for occluding an aperture within body tissue wherein the aperture includes an area of adequate rim and an area of inadequate rim.

Figure 1:
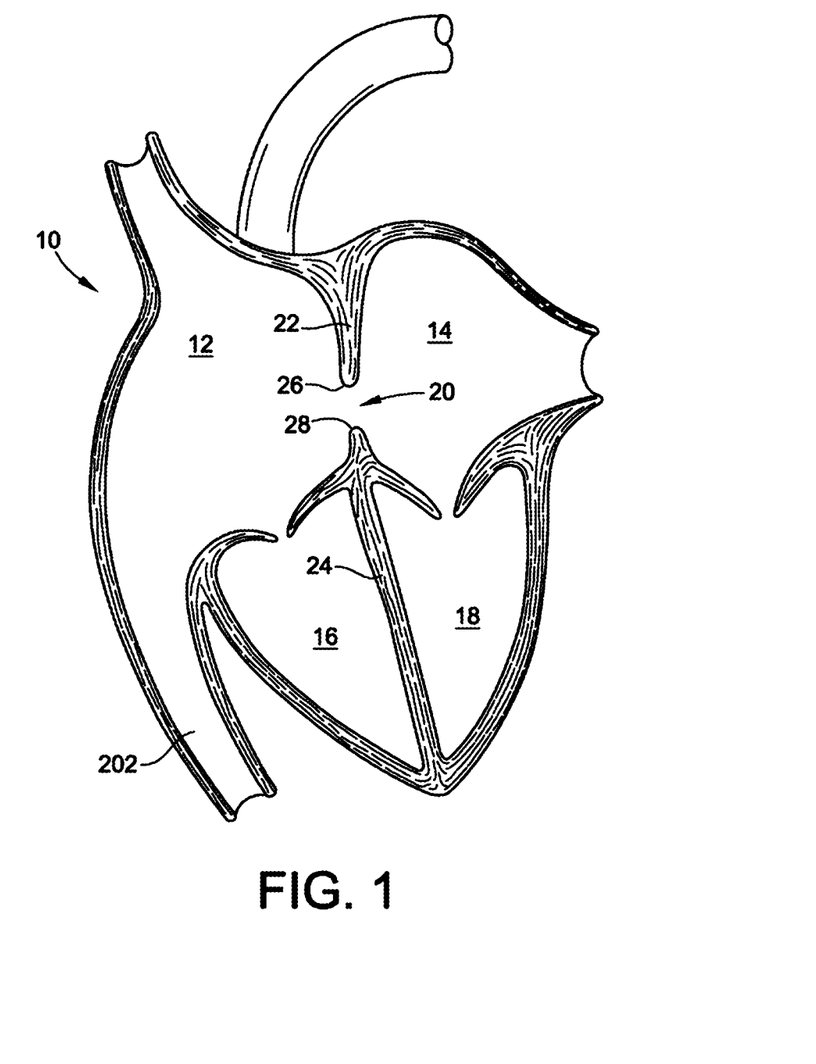
FIG. 1 is a schematic representation of a human heart illustrating an atrial septal defect (ASD).

FIG. 1 illustrates a human heart 10, having a right atrium 12, a left atrium 14, a right ventricle 16, and a left ventricle 18. Shown at 20 is an ASD anatomical anomaly or aperture in the atrial septum 22. The presence of an ASD 20 could permit blood to travel through septum 22, such as that schematically illustrated by aperture 20. A ventricle septal defect ("VSD") is similar to an ASD, except that an aperture would exist in the septum 24 between the right ventricle 16 and the left ventricle 18. Unless specifically described otherwise, the term "aperture" will refer to the specific heart defect described above, i.e., the ASD.

Occluder (or occlusion) devices are known for occluding ASDs. Reference is made to U.S. Patent Publication 2009/0228038 to Amin for one such heart occluder device. However, such devices are typically symmetrical occluders which are able to repair a defect having adequate rim structure completely encircling the defect. By "adequate rim structure," it is meant that there is a sufficient amount of tissue making up the rim and surrounding tissue of the heart wall to accept an occluder device.

Figure 2:
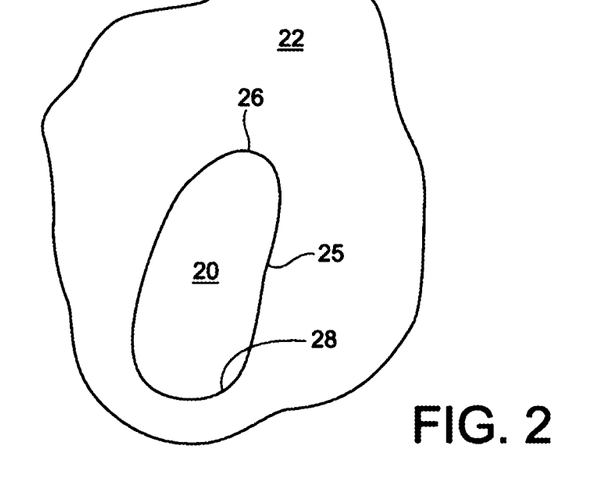
FIG. 2 is a schematic representation of the heart septum separating the right atrium (RA) from the left atrium (LA) and illustrating an ASD.

Unfortunately, there are times when the heart defect does not occur in a more centrally located area of the septum 22, but rather at the edge of the septum 22 as illustrated in FIG. 2. In these occurrences, the heart defect rim 25 is defined by a rim 26 of adequate surface structure to accept the heart occluder device and a rim 28 of inadequate surface structure, Where it will be difficult to accept the clamping mechanism of the heart occluder device with enough force to fix the heart occluder to the entire rim 25 structure of the heart defect. This situation requires a specialized form of heart occluder device as described in the present application.

As used herein, "distal" refers to the direction away from the delivery catheter and "proximal" refers to the direction nearer the delivery catheter.

As used herein, "memory" or "shape memory" refers to a property of materials to resume and maintain an intended shape despite being distorted for periods of time, such as during storage or during the process of delivery in viva.

Figure 3:
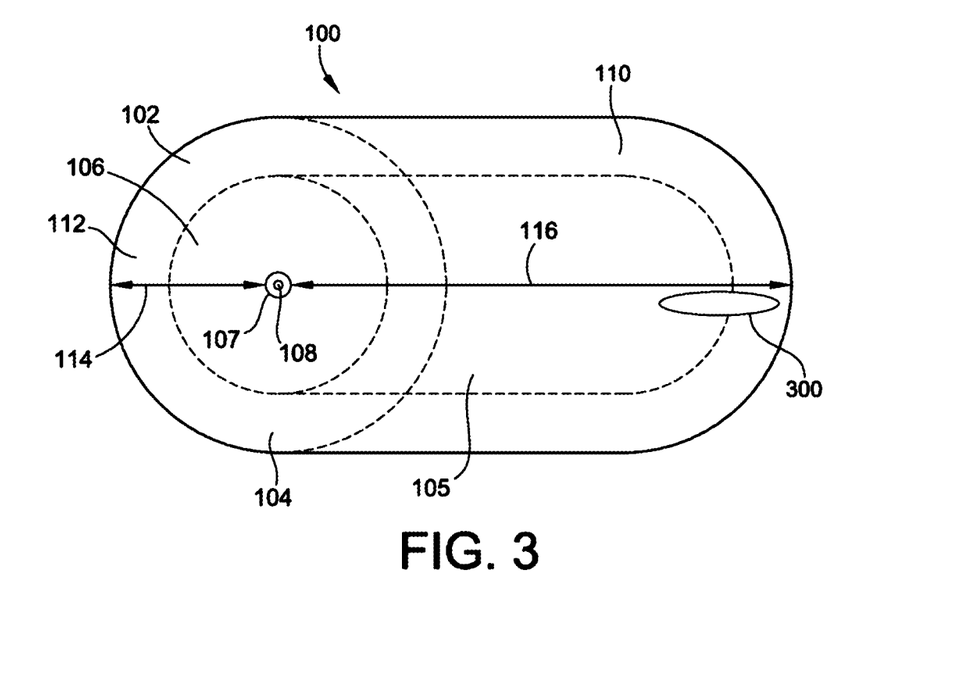
FIG. 3 is a top plan view illustrating the distinctions between the occluder device of the present invention and the prior art occluder device.

Reference is now made to FIG. 3, which illustrates the distinction between a standard, prior-art Amplatzer-type septal occluder 102, which is typically a self-centering device that consists of two circular retaining discs 104 (one shown in FIG. 3) made of nitinol wire mesh and linked together by a short connecting waist 106 surrounding a hub 107. The waist 106 centers the device 102 in the ASD and occludes it with the retaining discs 104 providing equal stability of the rim of the defect (Kasmouz, et al., 2013).

Figure 4:
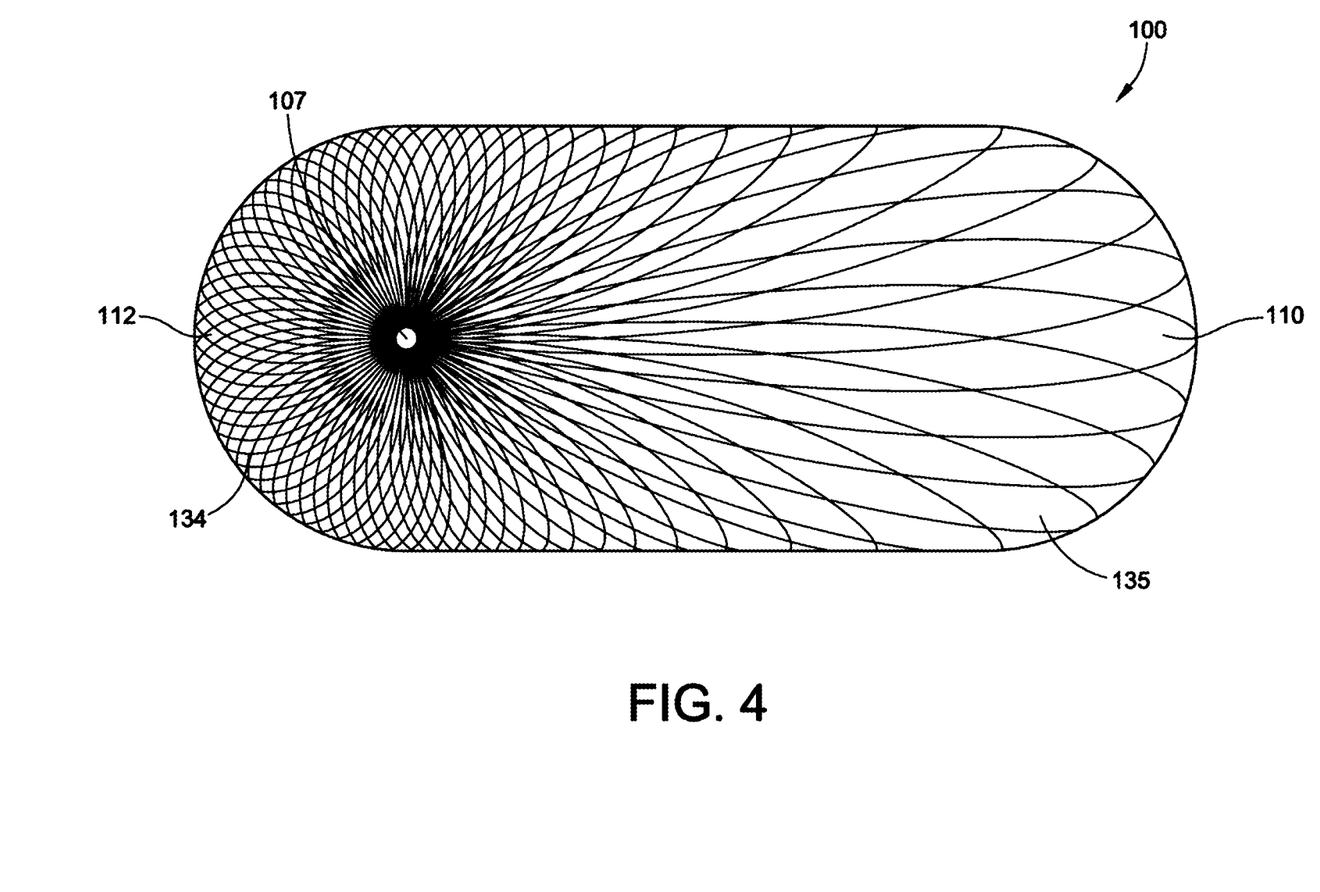
FIG. 4 is a top plan view of the occluder device of the present invention.
Figure 7:
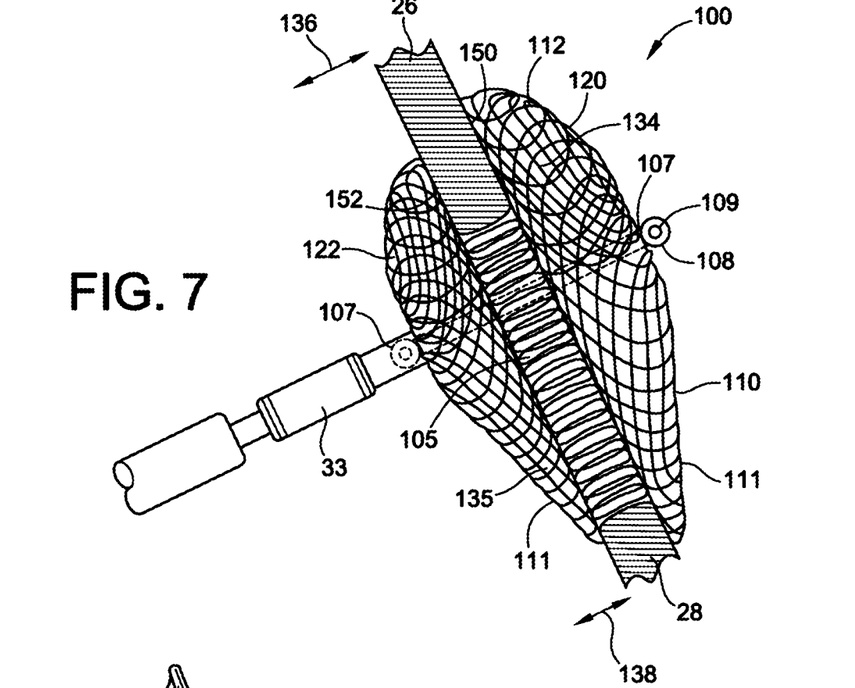
FIG. 7 is a side plan view illustrating the placement of the occluder device on the ASD.

Unlike the prior art occluder device 102 described above, the septal occluder device 100 of the present invention is distinguished by extended distal and proximal disks 120, 122 which include an extended arm 110 thereby giving each disk 120, 122 an ovoid or oval appearance. In addition, the waist 105 separating the disks 120, 122 is ovoid in shape to accommodate the shape of the disks 120, 122. The disks 120, 122 are further defined by having the hub area 107 offset thus forming a short arm 112 opposing the extended arm 110. As illustrated by arrows 114 and 116, the length or radius of the short arm 112 is shorter than the length or radius of the extended arm 110. As will be illustrated and described in this disclosure, the extended arm 110 in combination with the unique features of the short arm 112 will create a device for adequately occluding an aperture 20 in the heart septum 22 which is characterized by an inadequate rim structure 28. As illustrated in FIGS. 3, 4 and 7, the hub 107 is preferably defined by an extension 108 which includes a channel 109 passing through the extension 108. The usefulness of the channel 109 will become apparent in the description of the deployment, attachment and removal of the occluder device 100.

Figure 5:
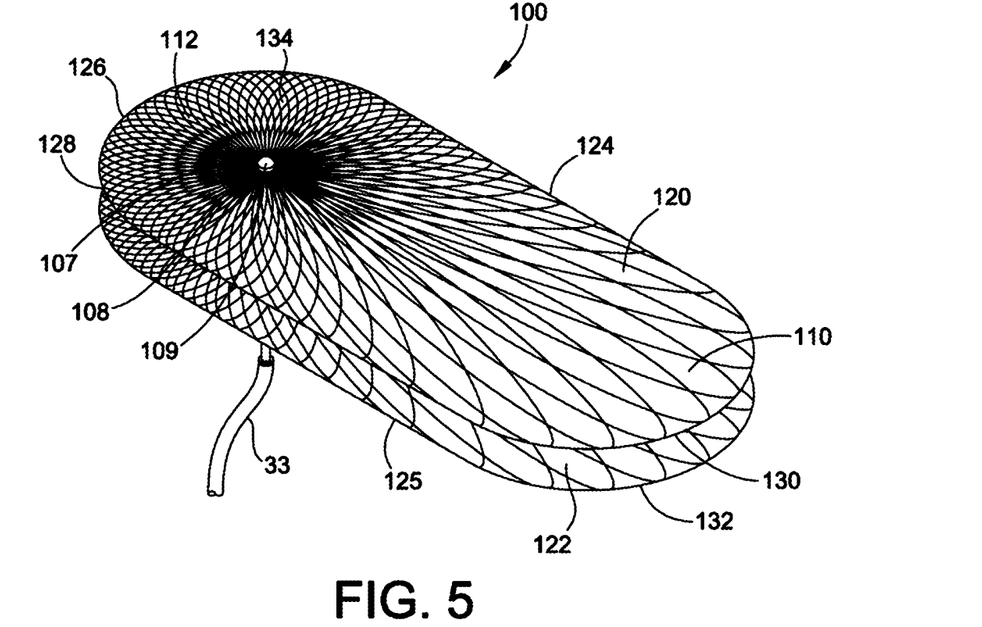
FIG. 5 is a perspective view of the occluder device of the present invention.

Referring now to FIGS. 4 and 5, the occluder device 100 of the present invention comprises two separate uniquely shaped ovoid disks, distal disk 120 and proximal disk 122, formed of shape memory material, such as wire or other specialized material. The material can be formed of biocompatible metals or polymers, such as bioresorbable polymers, shape memory polymers, shape memory metal alloys, biocompatible metals, bioresorbable metals, or combinations thereof. Specific examples include but are not limited to iron, magnesium, stainless steel, nitinol, or combinations of these and similar materials. A preferred metal for the present invention is a nitinol alloy. Nitinol (an acronym for Nickel Titanium Naval Ordnance Laboratory) is a family of intermetallic materials, which contain a nearly equal mixture of nickel (55 wt. %) and titanium. Other elements can be added to adjust or "tune" the material properties. Nitinol exhibits unique behavior, specifically, a well-defined "shape memory" and super elasticity. In general, any biocompatible material with a memory capability can be used with the present invention. The thermal shape memory and/or super-elastic properties of shape memory polymers and alloys permit the occluder 100 to resume and maintain its intended shape in viva despite being distorted during the delivery process.

In certain embodiments, the memory may also assist in pressing the aperture 20 closed. The diameter or thickness of the wire depends on the size and type of the device, i.e., the larger the device, the larger the diameter of the wire. In general, wire having a diameter between about 0.2 mm and 0.8 mm can be used.

Each disk 120, 122 in the occluder device 100 includes a rim 124, 126, also made of shaped memory material to create and hold the ovoid shape of each disk 120, 122 as illustrated. While the ovoid shape is illustrated and is the preferred shape for the device 100 of the present invention, it is within the scope to have other shapes as desired. Ideally, the shape of the disks 120, 122 is customized to approximate the size and shape of the ASD.

As illustrated primarily in FIG. 7, the size and shape of the distal occluder disk 120 is larger than the proximal occluder disk 122. Because the flow of blood naturally passes from the left atrium 14 to the right atrium 15, referred to FIG. 1, it is preferred but not absolutely necessary to enlarge the size of the distal occluder disk 120 to assist in blocking the flow of fluid and to prevent the occluder disk 100 from dislodging and passing into the right atrium 120 and possibly to the right ventricle 16 or pulmonary artery 202. For this reason, it is preferred to increase the overall size of the distal disk 120, in comparison to the proximal disk 122, to further secure the occluder disk 100 in position over the ASD.

The disks 120, 122 are shaped and constructed of a dense mesh of tightly woven wire material, such as nitinol. The form of the distal disk 120 opposes the form of the proximal disk 122 and is connected by a 3-4 mm short ovoid waist 105, illustrated in FIG. 7. The shape and relative size of the waist 105 preferably conforms to the shape and the size of the ASD 20. The disks 120, 122 are larger than the waist 105.

As illustrated in FIGS. 3 and 7, the waist portion 105 of the occluder device 100 is extended, ovoid and follows the contour of the disks 120, 122. The dimensions of the waist are variable, ranging from small to large, and are typically selected based on the size and shape of the ASD. Ideally, the waist 105 is formed to completely fill the ASD 20. The size of the waist 105 typically ranges between about 1 and 4 mm larger in size than the ASD 20, preferably between about 2 and 4 mm larger than the ASD. In this manner, the waist 105 can provide a stopper-like plug to the ASD 20 opening.

In addition to acting as a stopper for the ASD 20, the waist acts to retain the occluder disks 120, 122 in place on the ASD 20 for maximum sealing. Further, the waist 105 assists in preventing the inadvertent or accidental displacement of the occluder device 100.

The short arm 112 of each disk 120, 122 is defined by an arcuate portion 126, 128 in each rim 124, 125, and is designed to attach or clamp onto the rim 25 of the aperture 20 defined by the adequate rim 26.

Likewise, the extended arm 110 of each disk 120, 122 is defined by an arcuate portion 130, 132 in each rim 124, 125. This arm is intended to attach or clamp onto the rim 25 of the aperture 20 defined by the inadequate rim 28.

To assist in accomplishing this task, the short arm 112 is characterized by increased bulk or thickness density of memory material, illustrated by the dense mesh of memory material 134, to increase the size, structure, strength and tension of each disk 120, 122 at the region of the short arm 112. The added bulk can be accomplished by adding more memory material, such as memory wire, thicker wire, or a combination of both. Without wishing to be restricted to any set dimensions, the preferred thickness of the short arm, illustrated by arrow 136 in FIG. 7, is approximately twice the thickness of the extended arm 110, illustrated by arrow 138. The less dense memory material in extended arm 110 is designated by reference number 135.

Referring now to FIG. 7, the provision of a thicker, stronger, denser material 134 adds tension to the disks 120, 122 at the short arm 112. Clamping the disks 120, 122 onto the septum 22 at the area of the adequate rim 26 will then create a torsional rotation of the extended arms 110 of each disk 120, 122 along arrows 140, 142 in order to assist in a more secure attachment of the disks 120, 122 at the arcuate portion 130, 132 or precisely at the location of the inadequate rim 28. The torsional clamping effect will seat the occluder device 100 onto the rim 25 of the aperture 20 in a manner to prevent the device 100 from slipping off the aperture 20 at the area of the inadequate rim 28. In this manner, the occluding device 100 provides a firm gripping seal on the aperture 20 at the location of the adequate rim surface 26 and an enhanced gripping seal on the aperture 20 at the location of the inadequate rim surface 28. The "asymmetry" in thickness is therefore helpful in preventing the occluder device 100 from dislodging from the aperture 20.

It is also within the scope of the present invention to add a mild magnetic property to occluder device 100 at the short arm 112 of each disk 120, 122. The magnetic property is specifically placed on the wire mesh on the interior surfaces 150, 152 adjacent the adequate rim 26 area of the septum 20. Applying a mild magnetic property to each disk 120, 122 will aid in attracting each disk 120, 122 to each other for more secure closure over the adequate rim 26. This in turns adds closure pressure at the extended arm 110 portion of the disk thereby assisting the ends 130, 132 in a proper sealing closure on the inadequate rim 28. This effectively seals the aperture 20 without any displacement. Therefore, when both of the disks 120, 122 are deployed, the magnetic property causes the two disks 120, 122 to be kept attached to each other at the safe and firm part of the septum 22. As illustrated in FIG. 7, the mild magnetic property will be applied bilaterally to the atrial sides of both discs at the location of the short arm covering the adequate and firm rim. Therefore, after deployment, they will gently attach to each other.

Figure 13:
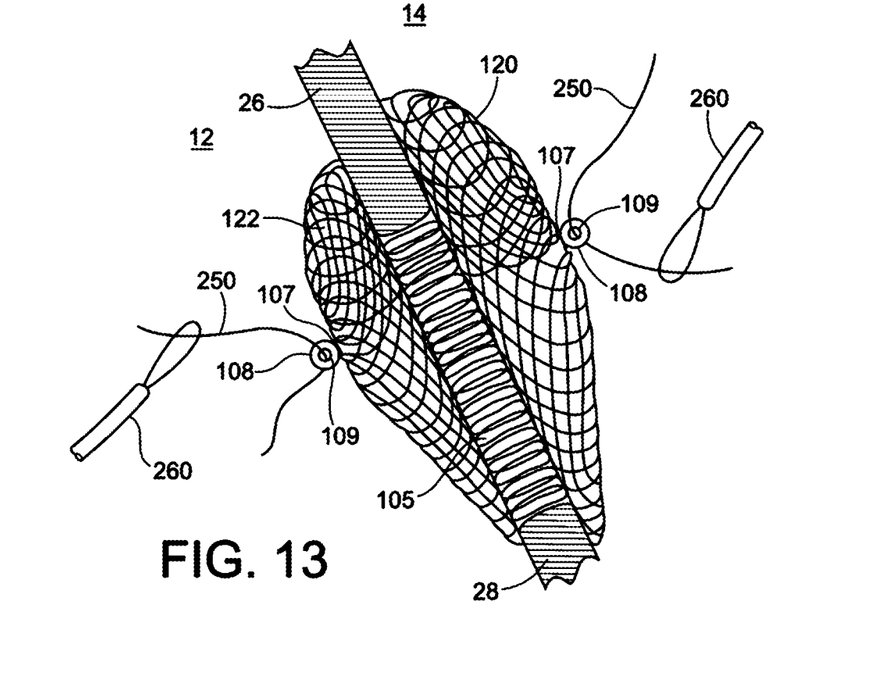
FIG. 13 is a close up side plan view illustrating the attachment of guide wires and a snare for the removal of the occluder device from the ASD.

Referring now to the hub 107 located in the center of the waist 105, the hub 107 is defined by an extension 108, located on both surfaces of the distal occluder disk 120 and proximal occluder disk 122. As illustrated in FIGS. 5, 7 and 13, the extension 108 includes a channel 109 extending through the extension 108. The channel 109 in the extension 109 is provided in order to remove the occluder device 100 if necessary. For example, the flow of blood from the left atrium 14 to the right atrium 12 in the heart 10 can dislodge the occluder device 100 if the device 100 is not adequately secure. This is called "embolism." Typically, the device 100 is dislodged toward the left atrium 14 and subsequently to the left ventricle 18 and aorta (not shown). Additionally, it is possible for the device 100 to be dislodged to the right ventricle 16 and the pulmonary artery 202. If the occluder device 100 becomes dislodged, causing an embolism, it will be necessary to remove the occluder device 100 from the heart 10. This can be accomplished by means of the channel 109 in the extension 108 as will be described later.

The occluder device 100 may also include a scaffold or sealed covering 111, illustrated in FIG. 7, over each of the distal and proximal disks 120, 122, wherein the covering provides a seal to occlude the ASD 20 wherein the coverings comprise a flexible, biocompatible material capable of promoting tissue growth and/or act as a sealant, including but not limited to polyester fabrics, Teflon-based materials or polyvinyl alcohol.

The deployment of the occluder device 100 is well-known to the art and similar to standard Amplatzer-type deployment steps. It is typically a percutaneous procedure which does not require major surgery.

Figure 8:
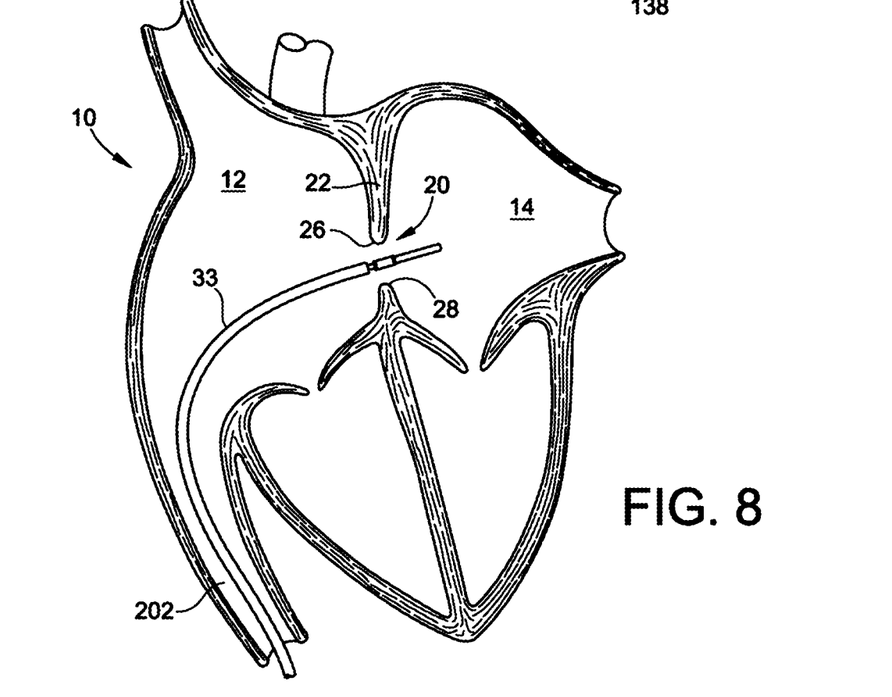
FIG. 8 is schematic view illustrating the initial placement of the occluder device through the ASD between the right atrium and the left atrium.

Referring to FIG. 8, the catheter 33 containing the occluder device 100 attached to the deployment cable 32, is fed Via a needle stick (not shown) through a large vein in the groin which feeds into the heart 100. The catheter 33 locates the ASD 20 and is passed through the ASD 20.

Figure 9:
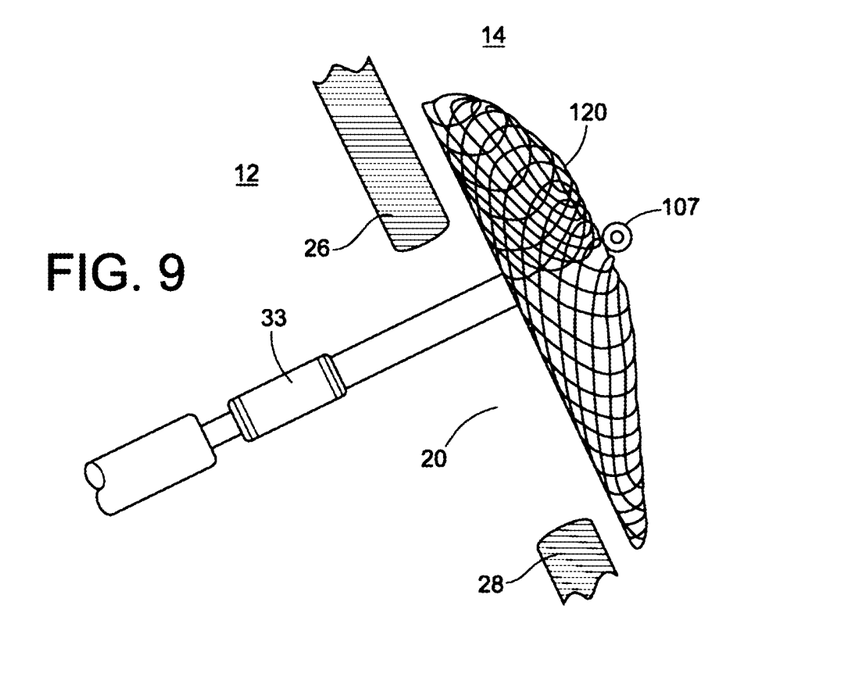
FIG. 9 is a close up side plan view illustrating the opening of the distal occluder disk in the region of the left atrium.

Referring to FIG. 9, the catheter 33 is withdrawn which allows the distal disk 120 to open and reform its memory shape in the left atrium 14. The distal disk 120 is then placed against the ASD 20 to seal off the ASD 20. The larger size of the distal disk 120, compared to the size of the proximal disk 122, assists in the proper placement of the distal disk 120 over the ASD 20. The radiomarker 300, housed within the occluder device 100, assists in the proper placement of the distal disk 120, by means known to the art. The distal disk 120 is positioned such that the arcuate portion 126 of the rim 124 in the short arm 112 is placed over the adequate rim 26 area of the ASD 20. As a result of this positioning the arcuate portion 130 of the distal disk is in proper placement over the inadequate rim area 28 of the ASD.

Figure 6:
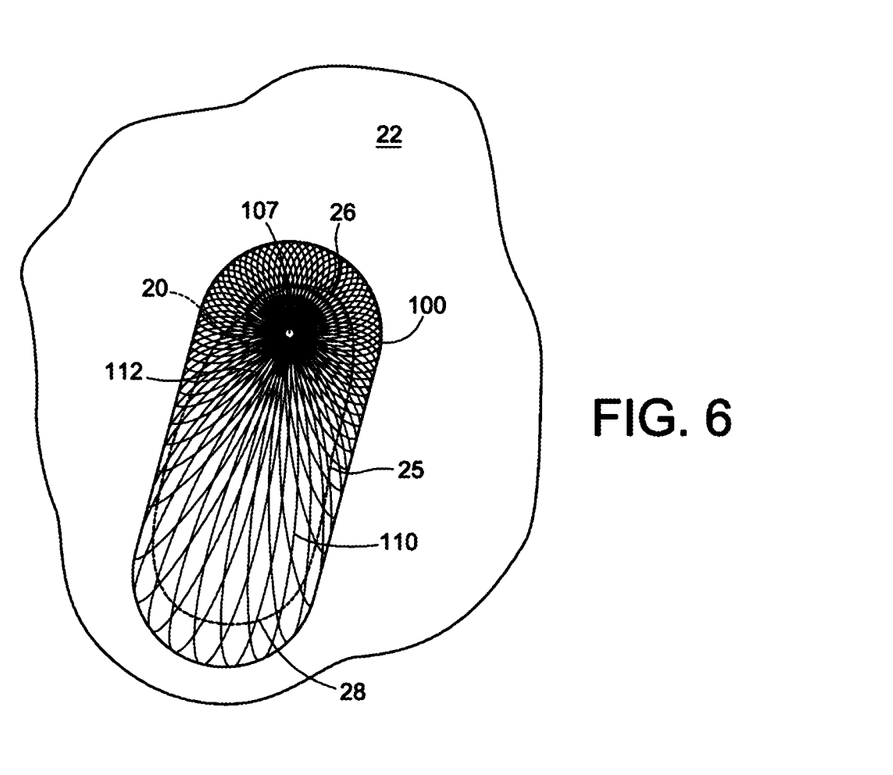
FIG. 6 is a top plan view illustrating the placement of the occluder device on the ASD.
Figure 10:
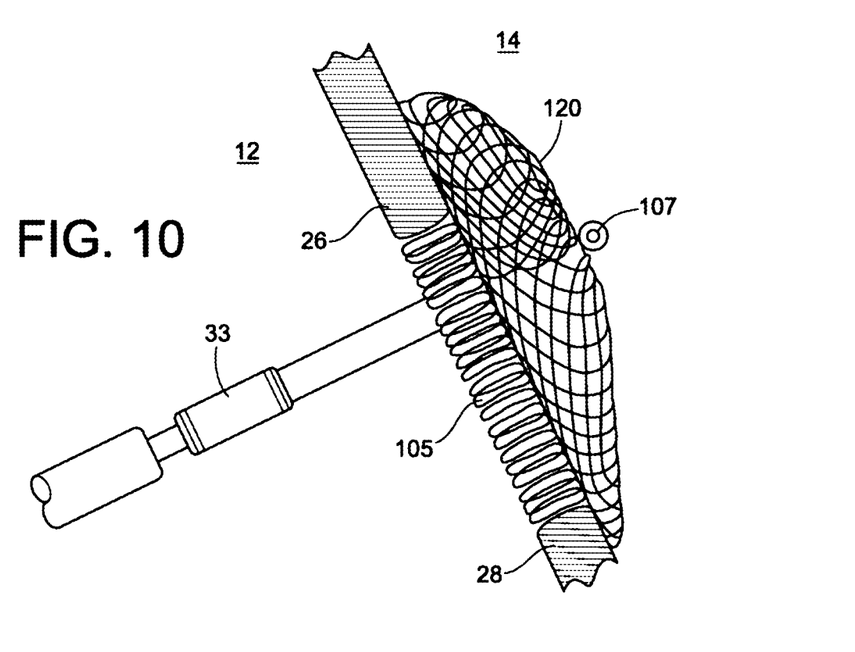
FIG. 10 is a close up side plan view illustrating the opening of the waist portion of the occluder disk.

Referring to FIGS. 6 and 10, once the distal disk 120 is properly positioned and secured against the rim 25 of the ASD 20, the catheter 33 is further withdrawn thereby revealing the waist 105 of the occluder 100. The waist 105 preferably fills and further plugs the entirety of the ASD 20.

Figure 11:
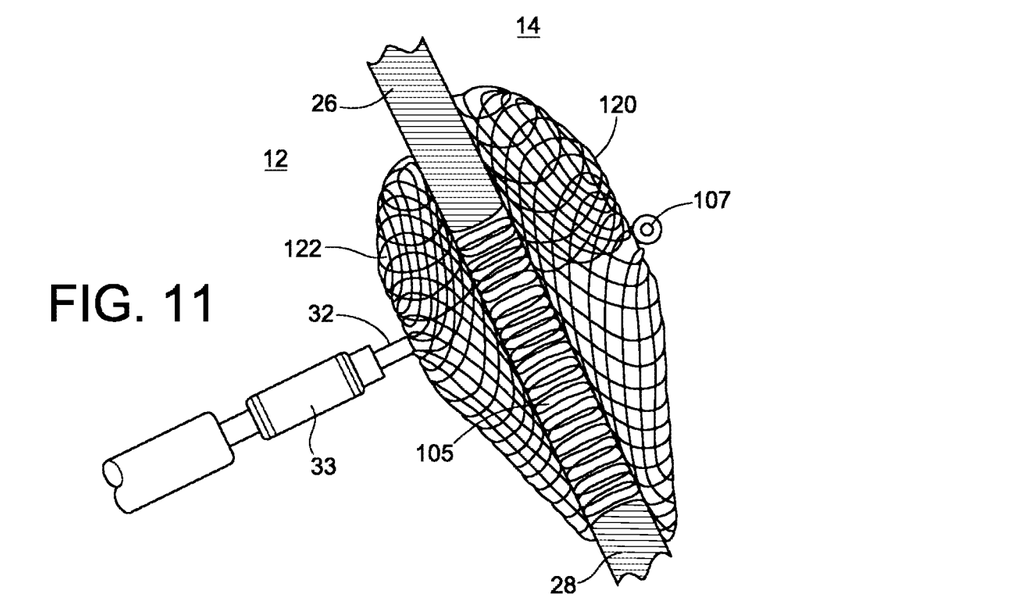
FIG. 11 is a close up side plan view illustrating the opening of the proximal occluder disk in the region of the right atrium.

Referring to FIG. 11, once both the distal disk 120 and the waist 105 are adequately secured over the ASD 20, the catheter 33 is further withdrawn revealing the proximal disk 122 in the right atrium 12. The proximal disk 122 is secured to the ASD 20 in the same position as the distal disk 120, such that the short arm 112 of the proximal disk 122 aligns with the short arm 112 of the distal disk 120. As illustrated in FIG. 7, a significant portion of the septum 22 at the adequate rim 26 area is positioned and essentially clamped between the short arms 112 of the distal and proximal disks 120, 122. Because of the unique properties of the short arms 112, i.e., its layer of denser memory material 134, the short arms 112 of both disks 120, 122 secure the occluder disk 100 to the ASD 20. In addition, the secured attachment of the short arms 112 assists in properly securing the extended arms 110 of each disk 120, 122 to the ASD 20 at the area of inadequate rim structure 28. Furthermore and as discussed previously, the short arms 112 of the disks 120, 122 can be provided with magnetic attraction at the interior surfaces 150, 152 of the short arms 112 to further assist in the clamping action of the short arms 112 of both disks 120, 122 on the ASD 20 at the area of adequate rim 26.

Figure 12:
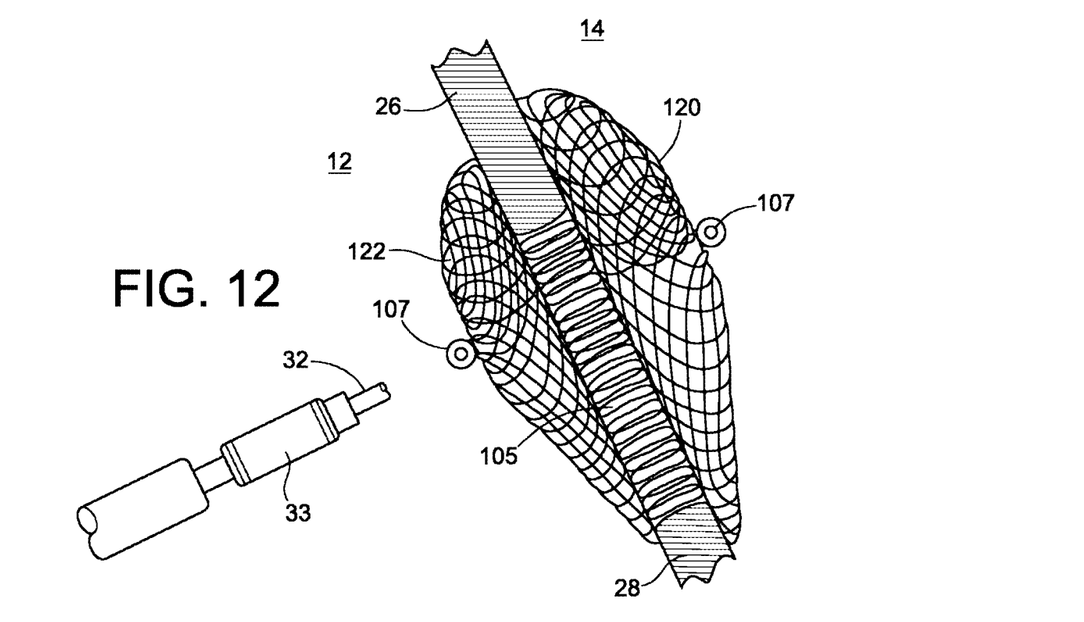
FIG. 12 is a close up side plan view illustrating the removal of the deployment cable and catheter from the occluder device.

Referring to FIG. 12, once the position of the occluder disk 100 is verified, the deployment cable 32, which secures the occluder device 100 to the catheter 33, is released by means known to the art, and the catheter 33 is removed by means known to the art.

Properly placed, the occluder device 100 will stay in place for the life of the patient. As the occluder device 100 becomes further embedded into the septum 22 tissue, new tissue will grow over the occluder device 100 further securing the occluder device 100 to the septum 22.

The occluder device 100 is connected to a hub 107, which includes a delivery attachment mechanism for attachment to a deployment cable 32 housed within a delivery catheter sheath or catheter 33.

Therefore, one, two or three of the following parameters can help the occluder device 100 seat properly in place without prolapse into the right atrium 12:

a. The extra length of the distal and proximal disks 120, 122 on the side with inadequate rim 28;

b. The added thickness or density of the short arms 112 of both the distal and proximal disks 120, 122; and c. The equal size of the distal and proximal disk members 120, 122 which provides better support, especially considering the firmer wire mesh and the larger retention disc member on part of the disc member that seats on the part of the septum 22 with the adequate rim 28.

In the event, the occluder device 100 must be removed for any reason, such as an inadvertent embolism, the channel 109 within the extension in the hub 108 in the occluder device 100 is useful for this process. The channel 109 within the extension 108 facilitates retrieving the occluder device 100 on both the left atrium 12 and right atrium 14 sides by passing an appropriate guide wire through the channel 109 and snaring the proximal disk 122.

Referring to FIG. 13, the extension 108 of either the distal disk 120 or the proximal disk 122 can receive a guide wire 250 which is threaded to the occluder device 100 Via an appropriate blood vessel. The guide wire 250 is snared by a snare wire 260, according to methods well known to the art, for retrieval of the occluder device 100.

Figure 14:
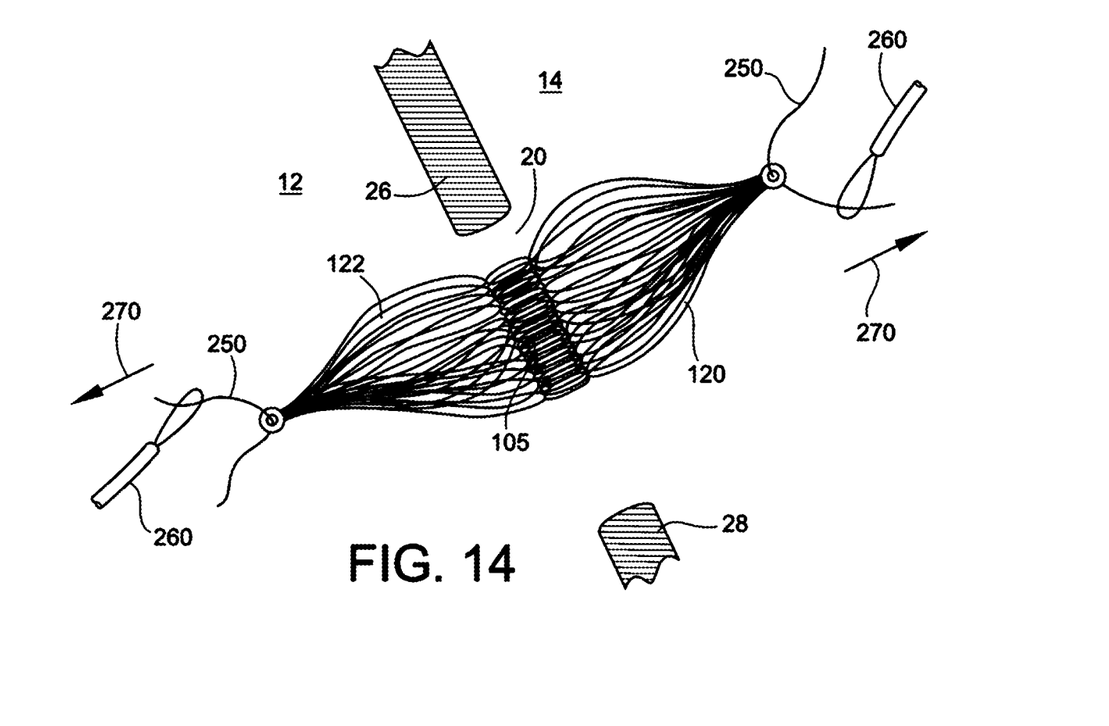
FIG. 14 is a side plan view illustrating the removal of the occluder device from the ASD.

Referring to FIG. 14, the snare wires 260, connected to the hubs 107 of both the distal and proximal disks 120, 122 can then be pulled along the direction of arrows 270 thereby stretching and pulling the occluder device 100 free from the ASD. In this stretched position, the occluder device 100 can be reinserted into a catheter 33 for removal from the heart 10 by means known to the art. Hydrophilic guide wires are preferred for this step.

Any version of any component or method step of the invention may be used with any other component or method step of the invention. The elements described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference in their entirety to the same extent as if each individual reference were specifically and individually indicated as being incorporated by reference. In case of conflict between the present disclosure and the incorporated references, the present disclosure controls.

The devices, methods, compounds and compositions of the present invention can comprise, consist of, or consist essentially of the essential elements and limitations described herein, as well as any additional or optional steps, ingredients, components, or limitations described herein or otherwise useful in the art.

While this invention may be embodied in many forms, what is described in detail herein is a specific preferred embodiment of the invention. The present disclosure is an exemplification of the principles of the invention is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

BIBLIOGRAPHY

Amin Z., "Transcatheter closure of secundum atrial septal defects," *Catheter Cardiovasc. Interv.,* 2006 November: 68(5):778-87. Review.

Gokaslan G., Ustunsoy H., Deniz H., Ozcaliskan O., Yasim A., Baspinar O. and G. Guzel, "Urgent surgical management for embolized occluder devices in childhood: single center experience," *J. Cardiothorac. Surg.,* 2012 Dec. 7; 7:127.

Kannan, B. R., Francis E., Sivakumar K., Anil S R. and R. K. Kumar, "Transcatheter closure of very large (> or =25 mm) atrial septal defects using the Amplatzer septal occluder," *Catheter Cardiovasc. Interv.,* 2003 August: 59(4):522-7.

Kazmouz, S., Kenny, D., Cao, Q., Kavinsky, C. J. and Z. M. Hijazi, "Transcatheter Closure of Secundum Atrial Septal Defects," *J. Invasive Cardiol.,* 2013; 25(5); 257-264.s King, T. D., Thompson, S. L., Steiner, C. and N. L. Mills, "Secundum Atrial Septal Defect: Nonoperative Closure During Cardiac Catheterization," *JAMA* 1976; 235 (23): 2506-2509.

King T. D. and N. L. Mills, Chapter 4: Historical perspectives on ASD device closure. In: Hijazi, Z. M.; Feldman, T., Al-Qbandi, M. A. and H. Sievert (eds) *Transcatheter Closure of ASDs and PFOs, A Comprehensive Assessment*, Minneapolis, Minn.: Cardiotext Publishing; 2010: 37-64.

Knirsch W., Dodge-Khatami A., Valsangiacomo-Buechel E., Weiss M. and F. Berger, "Challenges encountered during closure of atrial septal defects," *Pediatric Cardiology,* 2005: 26(2): 147-153.

Li G. S., Li H. D., Yang J., Zhang W. Q, Hou Z. S., Li Q. C. and Y. Zhang, "Feasibility and safety of transthoracic echocardiography-guided transcatheter closure of atrial septal defects with deficient superior-anterior rims," *PLoS One,* 2012 Dec. 17; 7(12):e51117.

Love B. A., Bock M. and S. Srivastava, "Advantages of the GORE® HELEX® Septal Occluder for Closure of Atrial Septal Defect with a Deficient Retroaortic Rim," *Closing Remarks,* 2012 Summer, XIX, 1-3, Gore Medical.

Moore J., Hegde S., E I-Said H., Beekman R. 3rd, Benson L., Bergersen L., Holzer R., Jenkins K., Ringel R., Rome J., Vincent R. and G. Martin, "Transcatheter device closure of atrial septal defects: a safety review," *JACC Cardiovasc. Interv.,* 2013 May: 6(5):433-42.

Podnar T., Martanovic P., Gavora P. and J. Masura, "Morphological variations of secundum-type atrial septal defects: feasibility for percutaneous closure using Amplatzer septal occluders," *Catheter Cardiovasc. Interv.,* 2001 July; 53(3):386-91.

What is claimed is:

1. A method of occluding a septal defect in a septum comprising:
    inserting a delivery catheter containing a septal occluder through the septal defect releasably attached to a hub in which wire ends of a braiding are gathered, said braiding forming a first disk and a second disk of said septal occluder, said first disk and said second disk joined together by a waist, and said hub is off-center of said waist, thereby creating a narrow portion on one side of the hub and a wide portion on an opposite side of the hub;
    expanding said first disk from a distal end of the catheter on a distal side of the septum;
    expanding said second disk from the distal end of the catheter on a proximal side of the septum, thereby squeezing the septum between the first disk and the second disk;
    wherein said off-center hub causes said delivery catheter to become displaced laterally from said septal defect prior to release;
    releasing said occluder from said delivery catheter by detaching from the catheter said hub.

2. The method of claim 1 further comprising providing an additional magnetic force between the first disk and the second disk.

3. The method of claim 1 wherein releasing the occluder comprises unthreading a snare wire that is threaded through an opening through the hub.

4. The method of claim 1 wherein expanding said second disk from the distal end of the catheter on a proximal side of the septum, thereby squeezing the septum between the first disk and the second disk comprises providing a torsional rotation of the first and second disk.

* * * * *